(12) United States Patent
Kim et al.

(10) Patent No.: US 7,166,718 B2
(45) Date of Patent: Jan. 23, 2007

(54) CALIX[4]ARENE-NUCLEOSIDE AND CALIX[4]OLIGONUCLEOTIDE HYBRIDS

(75) Inventors: Byeang Hyean Kim, Pohang-si (KR); Su Jeong Kim, Pohang-si (KR)

(73) Assignee: Postech Foundation (KR)

( * ) Notice: Subject to any disclaimer, the term of this patent is extended or adjusted under 35 U.S.C. 154(b) by 470 days.

(21) Appl. No.: 10/480,013

(22) PCT Filed: Jun. 19, 2002

(86) PCT No.: PCT/KR02/01160

§ 371 (c)(1),
(2), (4) Date: Dec. 4, 2003

(87) PCT Pub. No.: WO03/059925

PCT Pub. Date: Jul. 24, 2003

(65) Prior Publication Data

US 2004/0157794 A1    Aug. 12, 2004

(30) Foreign Application Priority Data

Jan. 15, 2002    (KR) .................................. 2002-2316

(51) Int. Cl.
*C07H 21/00* (2006.01)
*C07H 21/02* (2006.01)
*C07H 21/04* (2006.01)
*C08B 30/18* (2006.01)
*C08B 37/16* (2006.01)

(52) U.S. Cl. ................. 536/25.3; 536/22.1; 536/25.31; 536/28.1; 536/28.4; 536/28.53; 536/28.54

(58) Field of Classification Search ............... 536/22.1, 536/25.3, 25.31, 28.1, 28.4, 28.53, 28.54
See application file for complete search history.

(56) References Cited

OTHER PUBLICATIONS

Sidorov et al. Chem. Commun. (2000), pp. 2369-2370.*
Rudkevich et al. J. Org. Chem. (1994), vol. 59, pp. 3683-3686.*
Kim et al. Tetrahedron Letters (2002), vol. 43, pp. 6367-6371.*
Zeng et al. Tetrahedron (2003), vol. 59, pp. 2539-2548.*

* cited by examiner

*Primary Examiner*—Patrick Lewis
(74) *Attorney, Agent, or Firm*—Anderson Kill & Olick, PC (57) ABSTRACT

The present invention relates to calix[4]arene-nucleoside hybrids containing calix[4]arene moieties and calix[4]arene-oligonucleotide hybrids as a DNA hairpin structure mimics synthesized by using the calix[4]arene-nucleoside as a key building block. Calix[4]arene-nucleoside and calix[4]arene-oligonucleotide hybrids of the present invention can effectively recognize DNA or RNA through triplex formation by bonding between calix[4]arene containing cavity and biologically active substance.

15 Claims, 5 Drawing Sheets

```
PerSeptive Biosystems
8909 Expedite(TM) Nucleic Acid Synthesis System
Trityl Monitor
March 1, 2001 05:24:07 PM  Instrument: Expedite
________________________________________________________________________

Scale:     15 umole (Estimate)
Max Value: 2.51E6

CALIX[4]ARENE-NUCLEOSIDE AND CALIX[4]OLIGONUCLEOTIDE HYBRIDS

FIELD OF THE INVENTION

The present invention relates to calix[4]arene-nucleoside hybrids containing calix[4]arene moieties and to calix[4]arene-oligonucleotide hybrids synthesized as DNA hairpin structure mimics using the calix[4]arene-nucleoside hybrids.

BACKGROUND OF THE INVENTION

Preorganization and cooperativeness of multifunctional groups play a major role in biological reaction kinetics (A. R. Fersht, *Trends Biochem. Sci.* 28, 3111, 1987). Calix[4]arene is proposed as a promising host molecule due to the directional preorganization of functional binding groups and its capacity to cooperate the guest binding site rapidly by low energy conformational change (T. Harade, J. M. et al., *Tetrahedron* 49, 5941, 1993; J. Scheerder, et al., *Angew. Chem.* 108, 1172, 1996; *Angew. Chem. Int. Ed. Engl.* 35, 1090, 1996). Accordingly, it has been utilized as a building block for multifunctional enzyme models (P. Molenveld, et al., *J. Am. Chem. Soc.* 120, 6726, 1998). Recently, calix[4]arenes have been coupled with sugars (A. Dondoni, et al., *Tetrahedron Lett.* 42, 3295, 2001), amico acids (L. Frkanec, et al., *Chem. Eur. J.* 6, 442, 2000) and peptides (Y. Hamuro, et al., *Angew. Chem.* 109, 2797, 1997) to develop biologically active synthetic receptors or enzyme mimics. However, modified oligodeoxynucleotides (ODNs) containing calix[4]arene moieties are unprecedented.

The present inventors have endeavored to develop modified ODNs containing calix[4]arene moieties which can function as DNA hairpin structure mimics.

SUMMARY OF THE INVENTION

Accordingly, the primary object of the present invention is to provide calix[4]arene-nucleoside hybrids that may be used in the construction of calix[4]arene-oligonucleotide hybrids which can recognize oligonucleotides through interaction with biologically active compounds.

In accordance with one aspect of the present invention, there is provided a calix[4]arene-nucleoside hybrid containing at least one nucleoside attached to a calix[4]arene moiety through amide bonding, said moiety being derived from a calix[4]arene having one or more amino groups.

In accordance with another aspect of the present invention, there is provided a calix[4]arene-oligonucleotide hybrid having a moiety derived from the calix[4]arene-nucleoside hybrid and one or more nucleotide sequences respectively attached to the two nucleoside residue thereof.

BRIEF DESCRIPTION OF THE DRAWINGS

The above and other objects and features of the present invention will become apparent from the following description of the invention, when taken in conjunction with the accompanying drawings which respectively show.

DETAILED DESCRIPTION OF THE INVENTION

The present invention provides a calix[4]arene-nucleoside hybrid containing a calix[4]arene moiety as well as a calix[4]arene-oligonucleotide hybrid which mimics a DNA hairpin structure which is synthesized by using the calix[4]arene-nucleoside hybrid as a key building block.

The calix[4]arene used in the present invention has the structure as shown in a following formula 9.

<Formula 9>

Preferable nucleosides used in the present invention include, but are not limited to, adenosine and thymidine.

Figure 2:
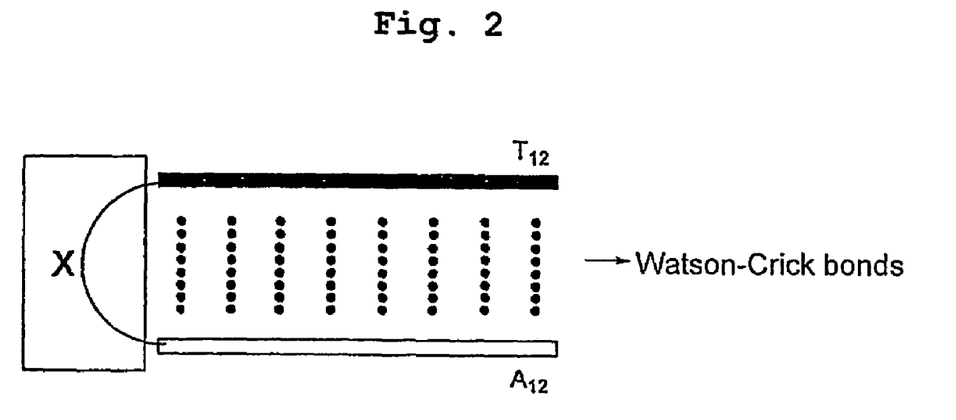
FIG. 2: the structure of the inventive calix[4]arene-oligonucleotide having the sequence of 5'-$A_{12}$-X-$T_{12}$-3' (X denotes the calix[4]arene-nucleoside 1)

According to one preferred mode of the present invention, there are provided calix[4]arene-nucleoside (hereinafter, calixnucleoside) hybrids of formula 1 to 4 which can each be used as a basic scaffold for constructing a DNA hairpin structure mimic, e.g., calix[4]arene-oligonucleotide (hereinafter, calixoligonucleotide) hybrid of 5'-$A_{12}$-X-$T_{12}$-3' (SEQ ID NO. 1, X denotes the calixnucleoside of formula 1), depicted in FIG. 2.

<Formula 1>

R = H, R' = H

<Formula 2>

R = TBDMS, R' = TBDPS

<Formula 3>

R = TBDMS

<Formula 4>

R = TBDPS

The inventive calixnucleoside and calixoligonucleotide hybrids are novel compounds and the calixoligonucleotide is a modified oligodeoxynucleotide (ODN) that has various structural advantages: it has a certain level of both rigidity and flexibility; it is stable in vivo and it has high cell permeability. Also, the inventive calixoligonucleotide can be easily mass-produced. Therefore, the inventive calixoilgonucleotide is useful as a hairpin type ODN which can recognize DNA or RNA through triplex formation (E. T. Kool, *Acc. Chem. Res.* 31, 502, 1998; S. Wang, et al., *Biochemistry* 34, 9774, 1995; E. Azhayeva, et al., *Nucleic Acid Res.* 23, 1170, 1995). ODNs have been shown to inhibit translation and transcription by binding to either single strand mRNA (antisense strategy) or double strand DNA (antigene strategy) (P. C. Zamecnik, et al., *Proc. Natl. Acad. Sci. U.S.A.* 75, 280, 1978; E. Uhlmann, et al., *Chem. Rev.* 90, 543, 1990). Effectuation of this idea in combating cancer and AIDS seems promising (A. D. Matteucci, et al., *Nature* 384, 20, 1996; D. H. Barton, et al., *Tetrahetron Lett.* 30, 4969, 1989). Therefore, the inventive calixnucleoside and calixoligonucleotide hybrids can be used for DNA sensor or gene therapy.

Also, the present invention provides a method for the preparation of calixnucleoside and calixoligonucleotide hybrids.

In the preferred embodiment of the present invention, it is described the synthetic details of four calixnucleoside hybrids using thymidine derivatives as nucleosides in Scheme 1.

<Scheme 1>

The key step of the calixnucleoside synthesis is the amide bond formation between the amine groups of calix[4]arene of formula 7 and the carboxylic acid group of thymidine nucleoside of formula 6 or 8.

For the activation of the 5'-acid functionality of the thymidine derivative of formula 6 (D. H. Barton, et al., *Tetrahedron Lett.* 30, 4969, 1989) in step (a) of Scheme 1, various peptide coupling reagents, such as (COCl)$_2$, EDC (1-(3-dimethylaminopropyl)-3-ethylcarbodiimide hydrochloride), TBC (2,4,6-trichlorobenzoylchloride) and TUTU (O-benzotriazole-1-yl-N,N,N',N'-tetramethyluronium tetrafluoroborate) can be used. For example, the use of TBTU provides a product having two identical thymidine residues (homo-coupled product), calixnucleoside of formula 3 in yield of 95%.

The thymidine derivative of formula 8 (J. Lebreton, et al., *Synlett.* 137, 1994; J. Y Kim, et al., *Nucleodises, Nucleotides & Nucleic Acids* 19, 637, 2000) may also be reacted with the 1,3-diaminocalix[4]arene compound of formula 7 (D. M. Rudkevich, et al., *J. Org. Chem.* 59, 3683, 1994) in a similar fashion (step c) to obtain the homo-coupled calixnucleoside of formula 4.

The calixnucleosides of formula 1 and 2 having two different thymidine residues (hetero-coupled products) may be synthesized with the mono-coupled calixnucleoside of formula 5 prepared as in step (b) by coupling the thymidine derivative of formula 6 (1.2 equiv) with 1,3-diaminocalix[4]arene of formula 7. Calixnucleoside of formula 2 is then produced by coupling the thymidine derivative of formula 8 with the mono-coupled calixnucleoside of formula 5 in step (d).

In step (e) of Scheme 1, the deprotected calixnucleoside of formula 1 may be prepared by removing R and R' from the calixnucleoside of formula 2 by the action of tetrabutylammonium fluoride.

The physical characteristics of the inventive calixnucleosides of formula 1 to 4 have been determined by elemental analysis, mass spectrometry, IR, $^1$H-NMR, $^{13}$C-NMR, UV, X-ray crystallography, polyacrylamide gel electrophoresis (PAGE), and circular dichroism (CD).

X-ray diffraction grade single crystals of the inventive calixnucleoside of formula 4 are grown by slowly evaporating a MeOH solution of the compound. The X-ray crystal structure confirms the structural assignment of the inventive calixnucleoside, and suggests that the two thymidine moieties are located in the same direction forming a U-shaped structure (see FIG. 1).

A calixoligonucleotide that mimics a DNA hairpin may be readily prepared by using the inventive calixnucleoside, e.g., by the following method.

First, a DMTr protected 2-cyanoethyl phosphoramidite building block of calixnucleoside of formula 1 is prepared and applied directly to solid phase oligonucleotide synthesis protocols on the PerSeptive Biosystems 8909 Expedite™ Nucleic Acid Synthesis System (M. J. Gait, *Oligonucleotide Synthesis* A Practical Approach. IRL Press, Oxford, Chapter 4, 1984). This provides as a DNA hairpin structure mimic, a modified ODN containing calixnucleoside of formula 1 in the middle of the sequence. The inventive calixoligonucleotide thus synthesized is designated oligo 1 and it has the sequence of 5'-$A_{12}$-X-$T_{12}$-3' (SEQ ID NO. 1, X denotes the calixnucleoside 1), which is depicted schematically in Structural formula 1 (see FIG. 2).

<Structural Formula 1>

Figure 3:
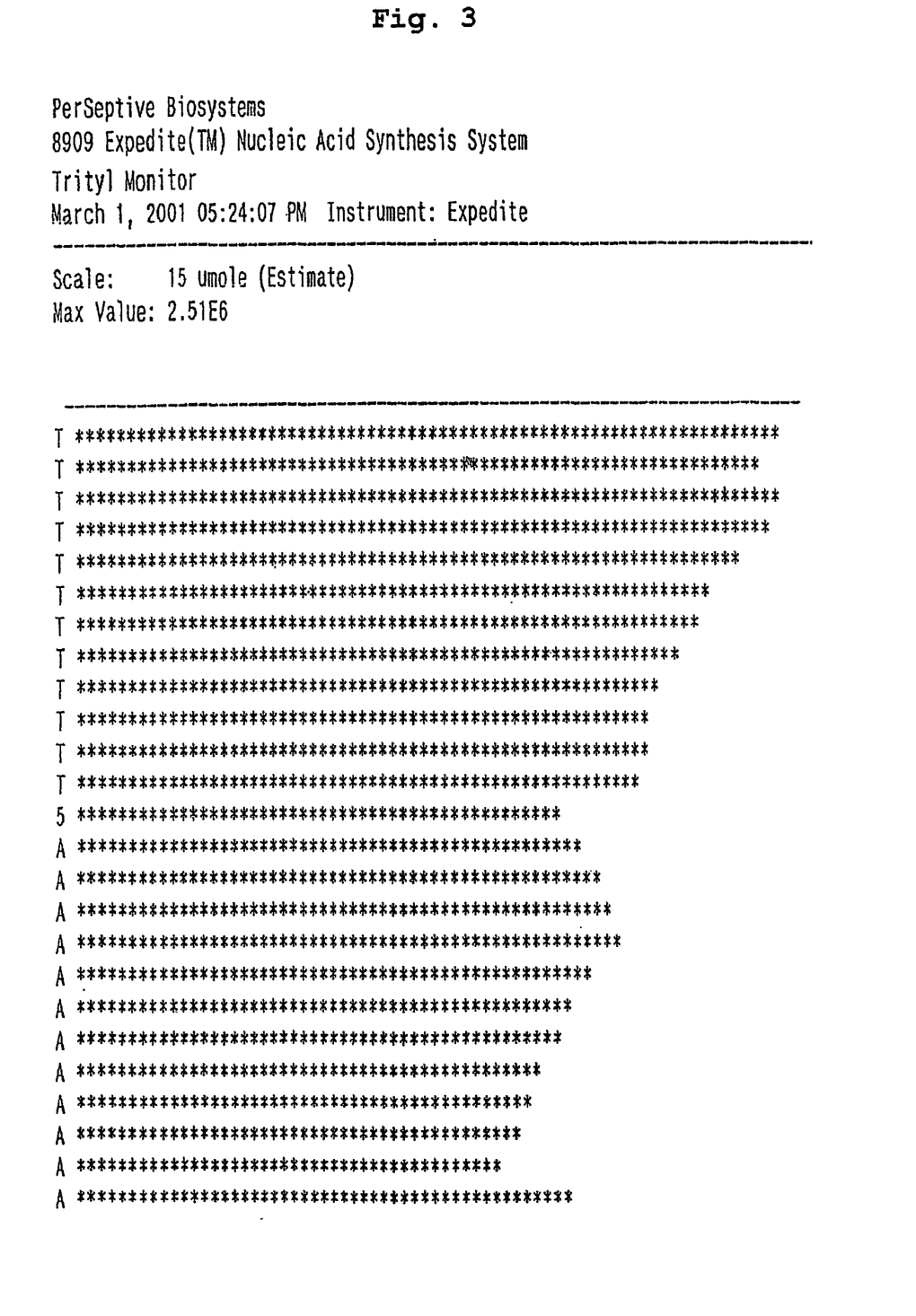
FIG. 3: DMTr cleavage data of the inventive calix[4]arene-oligonucleotide.

DMTr cleavage data of the above calixoligonucleotide have confirmed the attachment of the nucleotides to the calixnucleoside shown in FIG. 3. The inventive calixoligonucleotide may be purified by PAGE and reverse-phase HPLC, and the molecular weight thereof has been determined by matrix-assisted laser desorption/ionization time of fright (MALDI-TOF) mass spectrometry to be 8,539 (m/e).

Further, other calixoligonucleotide have been synthesized and purified: oligo 2 having the sequence of 5'-$T_{12}$-X-$T_{12}$-3' (SEQ ID NO. 2, X denotes the calixnucleoside 1) and oligo 3 having the sequence of 5'-AAAAGATATCAA-X-TTGACATCTTTT-3' (SEQ ID NO. 3, X denotes the calixnucleoside 1). Oligos 2 and 3 are depicted in Structural formula 2 and 3, respectively, and their molecular weights are determined to be 8,453 and 8,556 (m/e), respectively, by MALDI-TOF mass spectrometry.

<Structural Formula 2>

<Structural Formula 3>

Figure 4:
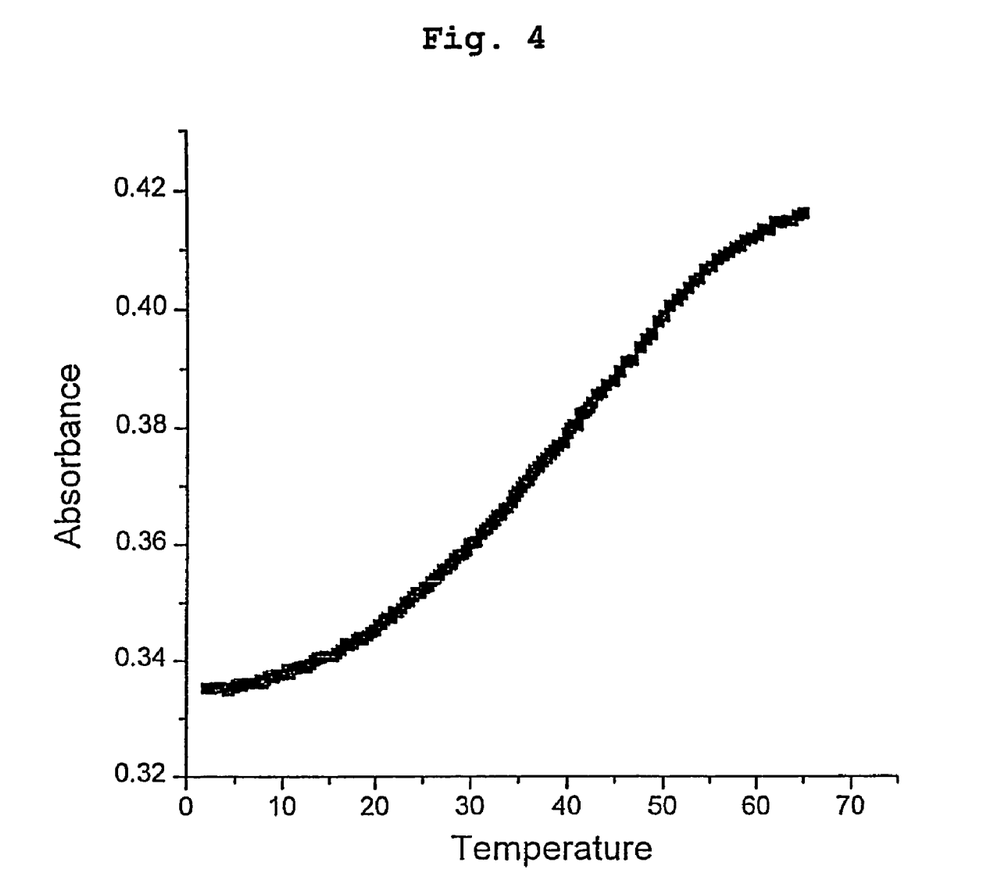
FIG. 4: thermal denaturation curve for the inventive calix[4]arene-oligonucleotide.

To verify the hairpin structure of the inventive calixoligonucleotide, the thermal denaturation behavior of oligo 1 has been examined by UV spectroscopy. The absorbance (at $\lambda_{260}$)-temperature plot is FIG. 4 shows a sigmoidal shape, wherein the midpoint corresponds to Tm value (40° C.) of the duplex. Thus, oligo 1 is confirmed to have a double helix structure formed through hydrogen bonding between complementary nucleo-bases (A and T), and hence, a DNA hairpin structure. Further evidence comes from CD spectrum of the inventive calixoligonucleotide (see FIG. 5). It has a positive band centred at 281 nm, a negative band centred at 249 nm, and the zero being around 260 nm. These CD data exhibit the distinct characteristics of B-form DNA (A. Rodger, et al., *Circular Dichroism & Linear Dichroism;* Oxford: Oxford University Press, pp. 24–29, 1997) and indicate that the inventive calixoligonucleotide adopts a DNA hairpin structure.

The following Examples and Test Examples are given for the purpose of illustration only, and are not intended to limit the scope of the invention.

EXAMPLE 1

Synthesis of Calixnucleoside Hybrids (Step 1) Synthesis of Calixnucleoside 3

The thymidine derivative of formula 6 (65 mg, 0.176 mmol, Samcheonri Chemical Ltd., D. H. Barton, et al., *Tetrahedron Lett.* 30, 4969, 1989), 2.4 equivalent based on the amount of the compound of formula 7, was mixed with TBTU (59 mg, 0.183 mmol, a peptide coupling agent), HOBT (26 mg, 0.194 mmol), 4-methylmorpholine (20 mg, 0.182 mmol), $CH_2Cl_2$ (6 ml), and reacted at room temperature for 30 min. The activated thymidine derivative was reacted with the compound of formula 7, 1.3-diaminocalix[4]arene, (49 mg, 0.079 mmol, Sigma-Aldrich, D. M. Rudkevich, et al., *J. Org. Chem.* 59, 3683, 1994) at room temperature for 4 hour to obtain the homo-coupled calixnucleoside of formula 3 in 69% yield.

(Step 2) Synthesis of Calixnucleoside 4

The thymidine derivative of formula 8 (652 mg, 1.247 mmol, Samcheonri Chemical Ltd., J. Lebreton, et al., *Synlett.* 137:b, 1994; J. Y. Kim, et al., *Nucleosides, Nucleotides & Nucleic Acids* 19, 637, 2000), 2.4 equivalent based on the amount of the compound of formula 7, was mixed with TBTU (400 mg, 1.247 mmol, a coupling agent), HOBT (84 mg, 0.624 mmol), 4-methylmorpholine (137 μl, 1.247 mmol), $CH_2Cl_2$ (15 ml), and reacted at room temperature for 30 min. The activated thymidine derivative was reacted with the compound of formula 7, 1.3-diaminocalix[4]arene, (311.4 mg, 0.5 mmol) at room temperature for 1 hour to obtain the homo-coupled calixnucleoside of formula 4 in 43% yield.

(Step 3) Synthesis of Calixnucleosides 1 and 2

The thymidine derivative of formula 6 (346 mg, 0.935 mmol), 1.2 equivalent based on the amount of compound of formula 7, was mixed with TBTU (450 mg, 1.40 mmol, a coupling agent), HOBT (126 mg, 0.935 mmol), 4-methylmorpholine (54 μl, 1.40 mmol), $CH_2Cl_2$ (15 ml), and reacted at room temperature for 30 min. The activated thymidine derivative was reacted with the compound of formula 7, 1.3-diaminocalix[4]arene, (612 mg, 0.935 mmol) at room temperature for 1 hour to obtain the mono-coupled calixnucleoside of formula 5 in 58% yield. The thymidine derivative of formula 8 (129 mg, 0.246 mmol) was activated by treating with TBTU (79 mg, 0.246 mmol), HOBT (17 mg, 0.123 mmol), 4-methylmorpholine (27 μl, 0.246 mmol), $CH_2Cl_2$ (10 ml) at room temperature for 30 min, and then, the calixnucleoside of formula 5 (110 mg, 0.113 mmol) synthesized above was added thereto and reacted at room temperature for 3 hour to obtain the calixnucleoside of formula 2 in 64% yield. The protecting groups of the calixnucleoside 2 (107.5 mg, 0.072 mmol) were then removed by treating with TBAF (75.2 mg, 0.288 mmol) in THF (10 ml) at room temperature for 10 min, to obtain the calixnucleoside of formula 1 in 83% yield.

EXAMPLE 2

Analysis of Physical Characteristics of Calixnucleosides 1 to 4

The physical characteristics of the inventive calixnucleosides prepared in Example 1 were determined by elemental analysis, mass spectrometry, IR, $^1$H-NMR, $^{13}$C-NMR, UV, X-ray crystallography, polyacrylamide gel electrophoresis (PAGE), and circular dichroism (CD) as follows:

Calixnucleoside 1 m.p.: >212.5° C. (decomp); MS (FAB): m/z: 1127.6 (M+H$^+$); $[\alpha]^{20}$D=+6.70 (c=0.0094 in $CHCl_3$); IR (neat): ν=3309, 3065, 2961, 2931, 2875, 1682, 1465 cm$^{-1}$; $^1$H NMR (300 MHz, [D$_6$]Acetone/CDCl$_3$ 1/1 (v/v)): δ=10.05 (s, 1H), 9.88 (s, 1H), 9.02 (s, 1H), 8.66 (s, 1H), 7.94 (s, 1H), 7.92 (s, 1H), 7.66 (s, 1H), 6.90 (s, 1H), 6.84 (s, 1H), 6.79 (s, 1H), 6.65–6.45 (m, 7H), 6.31 (dd, 1H), 6.01 (dd, 1H), 5.39 (s, 1H), 4.85 (br, 1H), 4.57 (br, 1H), 4.40 (s, 2H), 4.35 (s, 2H), 4.34 (m, 1H), 4.22 (br, 1H), 3.87 (m, 1H), 3.77 (m, 9H), 3.07 (t, J=13.8 Hz, 4H), 2.75 (m, 1H), 2.47 (m, 2H), 2.32 (m, 2H), 2.22 (m, 2H), 1.88 (br, 11H), 1.80 (s, 3H), 0.94 (q, J=3.6 Hz, 12H); $^{13}$C NMR (75.5 MHz, [D$_6$]Acetone/CDCl$_3$ 1/1 (v/v)): δ=169.9, 168.6, 164.5, 164.2, 156.8, 153.8, 153.5, 151.4, 150.9, 135.6, 135.5, 135.2, 132.5, 132.1, 128.5, 122.4, 120.8, 111.2, 109.7, 88.7, 87.1, 86.7, 85.1, 77.1, 77.0, 75.0, 61.6, 39.5, 38.5, 38.1, 33.9, 31.3, 23.5, 12.6, 10.6, 10.5; Elemental analysis: $C_{62}H_{74}N_6O_{14}$, Calcd: C, 66.06; H, 6.62; N, 7.45. Found: C, 65.75; H, 6.97; N, 7.73.

Calixnucleoside 2 m.p.: 176.4–178.2° C.; MS (FAB): m/z: 1479.3 (M+H$^+$); $[\alpha]^{23}$D=+16.8 (c=0.0079 in $CH_2Cl_2$); IR(neat): ν=3306, 3066, 2958, 2931, 2958, 1694, 1552, 1468 cm$^{-1}$; $^1$H NMR (300 MHz, [D$_6$]Acetone): δ=10.23 (s, 1H), 9.95 (s, 1H), 9.46 (s, 1H), 8.97 (s, 1H), 7.84 (s, 1H), 7.79–7.75 (m, 4H), 7.54 (d, J=1.0 Hz, 1H), 7.48 –7.37 (m, 8H), 7.28 (d, J=3.6 Hz, 2H), 6.40–6.33 (m, 6H), 6.27 (dd, J1=5.3 Hz, J2=9.3Hz, 1H), 6.20 (dd, J1=4.9 Hz, J2=7.0 Hz, 1H), 4.79 (d, J=5.0 Hz, 1H), 4.49 (d, J=3.8 Hz, 2H), 4.45 (d, J=3.8 Hz, 2H), 4.38 (d, J=1.3 Hz, 1H), 4.09 (dd, J1=7.7 Hz, J2=9.0 Hz, 1H), 4.00–3.95 (m, 6H), 3.76 (t, J=7.0 Hz, 4H), 3.15 (d, J=8.0 Hz, 2H), 3.11 (d, J=6.7 Hz, 2H), 3.01 (q, J=7.7 Hz, 1H), 2.63–2.48 (m, 2H), 2.42–2.18 (m, 3H), 1.96 (m, 8H), 1.87 (s, 3H), 1.56 (d, J=0.9 Hz, 3H), 1.09 (m, 15H), 0.96 (m, 15H), 0.20 (s, 3H), 0.19 (s, 3H); $^{13}$C NMR(75.5 MHz, [D$_6$] Acetone): δ=170.0, 168.9, 164.6, 157.0, 155.1, 154.7, 152.4, 151.7, 139.9, 137.6, 137.5, 136.9, 136.8, 136.7, 135.0, 134.9, 134.5, 133.8, 131.2, 129.2, 129.0, 123.3, 121.5, 121.3, 111.8, 111.2, 90.9, 88.7, 86.6, 85.4, 78.1, 78.0, 77.3, 65.8, 40.7, 39.4, 39.0, 36.5, 32.2, 27.9, 26.7, 24.6, 24.3, 20.5, 19.1, 13.0, 12.9, 11.5, 10.9, −4.1, −4.2; Elemental analysis: $C_{84}H_{106}N_6O_{14}Si_2$, Cald: C, 68.17; H, 7.21; N, 5.67. Found: C, 67.79; H, 7.53; N, 5.85.

Calixnucleoside 3 m.p.: 212.3–214.2° C.; MS (FAB): m/z: 1327.3 (M+H$^+$); $[\alpha]^{24}$D=−9.42 (c=0.0046 in $CH_2Cl_2$); IR(neat): ν=3284, 3063, 2957, 2930, 2857, 1682, 1466 cm$^{-1}$; $^1$H NMR(300 MHz, CDCl$_3$): δ=9.02 (s, 2H), 8.95 (s, 2H), 7.37 (d, J=2.2 Hz, 2H), 7.17 (s, 4H), 6.27 (s, 6H), 6.00 (dd, J1=4.9 Hz, J2=9.8 Hz, 2H), 4.72 (d, J=4.5 Hz, 2H), 4.41 (d, J=4.2 Hz, 4H), 4.37 (s, 2H), 3.91 (t, J=7.8 Hz, 4H), 3.67 (t, J=6.9 Hz, 4H), 3.14 (d, J=4.6 Hz, 2H), 3.09 (d, J=4.6 Hz, 2H), 2.72 (m, 2H), 2.04 (dd, J1=5.0 Hz, J2=12.7 Hz, 2H), 1.96–1.80 (m, 14H), 1.04 (t, J=7.3 Hz, 6H), 0.92 (s, 18H), 0.88 (t, J=7.5 Hz, 6H), 0.18 (s, 6H), 0.15 (s, 6H); $^{13}$C NMR(75.5 MHz, CDCl$_3$): δ=167.5, 163.8, 155.6, 154.8, 150.7, 138.9, 137.1, 137.1, 133.5, 133.5, 131.4, 127.8, 122.3, 120.5, 111.9, 110.8, 91.8, 87.8, 77.1, 75.8, 37.4, 31.2, 26.0, 23.6, 23.1, 18.2, 12.6, 10.9, 10.2, −4.5, −4.7; Elemental analysis: $C_{72}H_{98}N_6O_{14}Si_2 \cdot 3H_2O$, Cald: C, 62.58; H, 7.58; N, 6.08. Found: C, 62.92; H, 7.65; N, 5.84.

Calixnucleoside 4 m.p.: 222.4–223.7° C.; MS (FAB): m/z: 1630.5 (M$^+$); $[\alpha]^{24}$D=+9.27 (c=0.0035 in $CH_2Cl_2$); IR (neat): ν=3314, 3068, 2960, 2931, 2873, 1688, 1605, 1544, 1468 cm$^{-1}$; $^1$H NMR(300 MHz, CDCl$_3$/CD$_3$OD 15/1 (v/v)): δ=10.5 (br, 2H), 8.46 (br, 2H), 7.59 (s, 2H), 7.41 (s, 2H), 7.34–7.24 (m, 12H), 6.80 (s, 2H), 6.75 (s, 2H), 6.51 (d, J=7.1 Hz, 4H), 6.42 (t, J=7.1 Hz, 2H), 6.05 (t, J=5.8 Hz, 2H), 4.36 (d, J=13.2 Hz, 4H), 3.94 (d, J=7.8 Hz, 2H), 3.75 (s, 10H), 3.30 (s, 1H), 3.17 (s, 1H), 3.05 (d, J=13.3 Hz, 4H), 2.84 (br, 2H), 2.34–2.03 (m, 8H), 1.84 (q, J=7.2 Hz, 8H), 1.49 (s, 6H), 1.01 (s, 18H), 0.91 (dd, J1=7.6 Hz, J2=16.2 Hz, 12H); $^{13}$C NMR(75.5 MHz, CDCl$_3$/CD$_3$OD 15/1 (v/v)): δ=169.2, 164.5, 156.4, 153.7, 150.9, 135.7, 135.7, 135.4, 134.7, 133.3, 132.7, 131.6, 130.1, 130.0, 128.4, 128.1, 128.0, 128.0, 122.1, 120.6, 120.5, 111.2, 85.3, 84.6, 76.9, 64.5, 39.7, 38.2, 35.5, 31.1, 27.0, 23.3, 23.2, 19.5, 12.0, 10.4, 10.3; Elemental analysis: $C_{96}H_{114}N_6O_{14}Si_2 \cdot 2H_2O$, Cald: C, 69.12; H, 7.13; N, 5.04. Found: C, 69.19; H, 7.13; N, 4.81.

Figure 1:
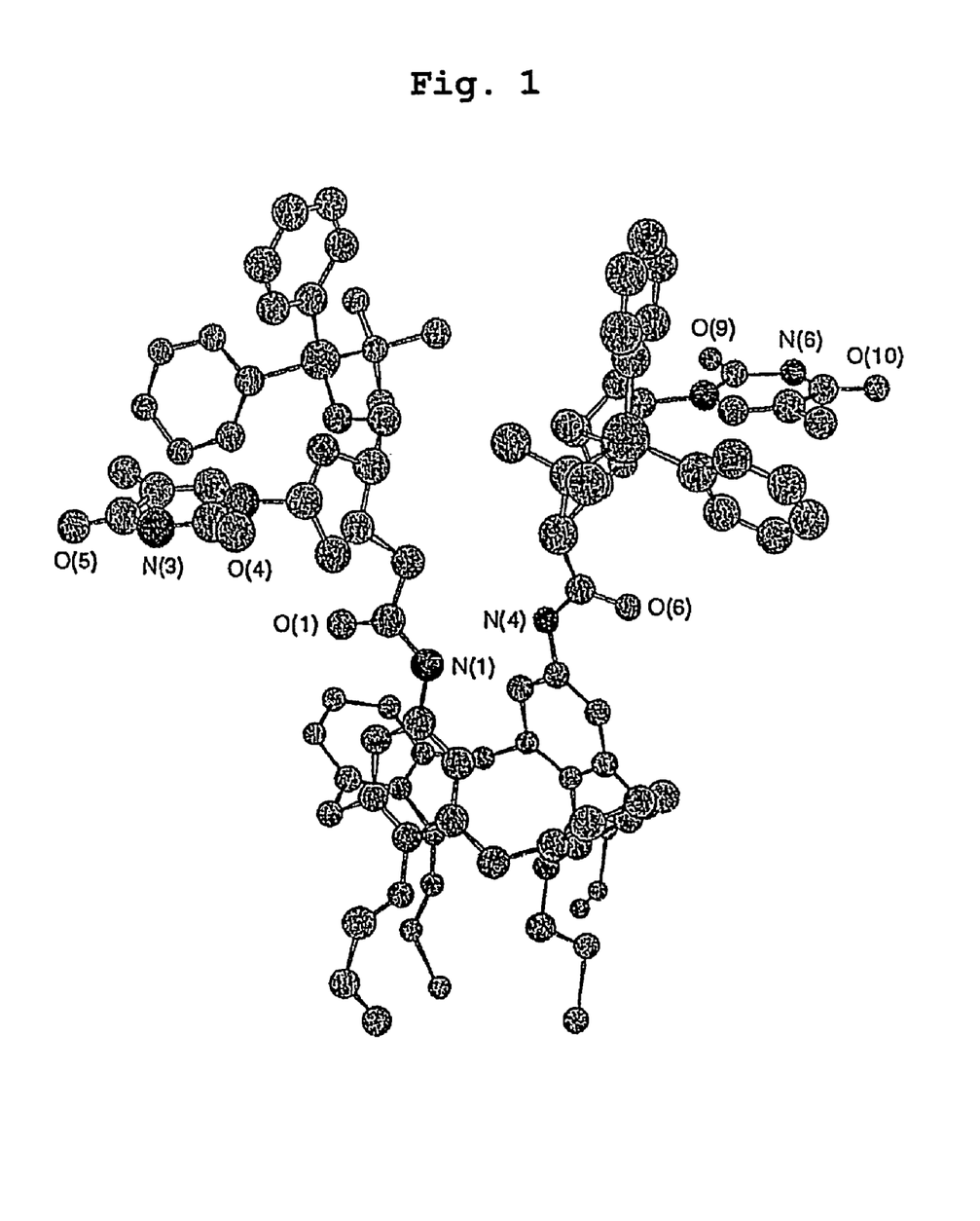
FIG. 1: the X-ray crystal structure (Chem SD rendering) of the inventive calix[4]arene-nucleoside 4.

As illustrated in FIG. 1, X-ray crystal data confirmed the structural assignment of the inventive calixnucleoside.

min, 24.2 μl of chloro[diisopropylamino]-β-cyanoethoxyphospine (0.16 mmol) was added thereto, and reacted for 1 hour to obtain DMTr protected 2-cyanoethyl phosphoramidite building block in 74% yield.

(Step 2) Synthesis of Calixoligonucleotide Hybrid

The DMTr protected 2-cyanoethyl phosphoramidite building block synthesized in Step 1 was applied to solid phase oligonucleotide synthesis protocols on the PerSeptive Biosystems 8909 Expedite™ Nucleic Acid Synthesis System (M. J. Gait, *Oligonucleotide Synthesis* A Practical Approach. IRL Press, Oxford, Chapter 4, 1984). To mimic on DNA hairpin structure, a modified ODN containing calixnucleoside 1 in the middle of sequence was synthesized. The calixoligonucleotide thus synthesized has the sequence of 5'-$A_{12}$-X-$T_{12}$-3' (SEQ ID NO. 1, X denotes the calixnucleoside 1), and the structure shows below (FIG. 2):

<Structural Formula 1>

EXAMPLE 3

Synthesis of Calixoligonucleotide Having a DNA Hairpin Structure (Step 1) Preparation of 2-cyanoethyl phosphoramidite Building Block DMTr protected 2-cyanoethyl phosphoroamidite building block of calixnucleoside 1 was prepared by the method according to Agrawal, S. (Methods in Molecular Biology Protocols foroligonucleotides and analogs; synthesis and properties. Totowa, N.J. p42, 1993); as follows.

Calixnucleoside 1 (325 mg, 0.289 mmol) was mixed with DMTr-Cl (221 mg, 0.650 mmol), Et$_3$N (91 μl, 0.65 mmol), pyridine (10 ml), and reacted at room temperature for 6 hour to obtain DMTr protected calixnucleoside 1. After the DMTr protected calixnucleoside (129 mg, 0.09 mmol) was dissolved in THF 5 ml, DIPEA (22 μl, 0.14 mmol) was added thereto. The mixture was agitated at room temperature for 30

As illustrated in FIG. 3, DMTr cleavage data confirmed that the inventive calixoligonucleotide prepared above had the identified nucleotides attached to the calixnucleoside. The inventive calixoligonucleotide was loaded on 20×20 cm PAGE gel and subjected to successive runnings at 200 V for 8 hour and 300 V for 2 hour. The gel was dissolved in 7 ml of distilled water and extracted at 30° C., 200 rpm for 12 hour. The gel was removed by filtering, and the extract solution was concentrated by distillation. The residue was then dissolved in 1 ml of distilled water, and purified by reverse-phase HPLC (conditions: column 10 mm×250 mm ODS; CH$_3$CN/0.1 M, TEAA=95/5 solution A; CH$_3$CN/0.1 M, TEAA=50/50 solution B; 0~10, 10~10, 20~100, 25~100, 30~10 of gradient (min-% of solution B); 3 ml/min of flow rate; 20~24 min of retention time). The molecular weight of the purified calixoligonucleotide was determined by matrix-assisted laser desorption/ionization time of fright (MALDI-TOF MS, substrate: 3-hydroxypicolic acid, Positive Mode) mass spectrometry to be 8,539 (m/e).

EXAMPLE 4

Structural Analysis of Calixoligonucleotide (4-1) Thermal Denaturation Experiment To verify the hairpin structure of the inventive calixoligonucleotide (oligo 1), a thermal denaturation experiment was carried: The calixoligonucleotide (0.35 OD, 10.5 µg) was dissolved in 10 mM Tris-HCl buffer (pH 7.2, [NaCl] =1.0 M), heated at 75° C. for 5 min, and slowly cooled to room temperature. Then, the change in the absorbance at 260 nm with temperature was monitored with a UV spectrophotometer (UV-2501PC Spectrophotometer, Shimazu).

As shown in FIG. 4, the curve of obtained by plotting absorbance against temperature reveals a sigmoidal shape, wherein the midpoint represents Tm value (40° C.) of the duplex.

(4-2) CD Spectrum Analysis

CD spectrum (circular dichroism spectrum) analysis was performed with a spectropolarimeter (Jasco J715 Spectropolarimeter) under the condition of pH 7.0, 10 mM Tris-HCl buffer, 100 mM NaCl and 20 mM $MgCl_2$.

Figure 5:
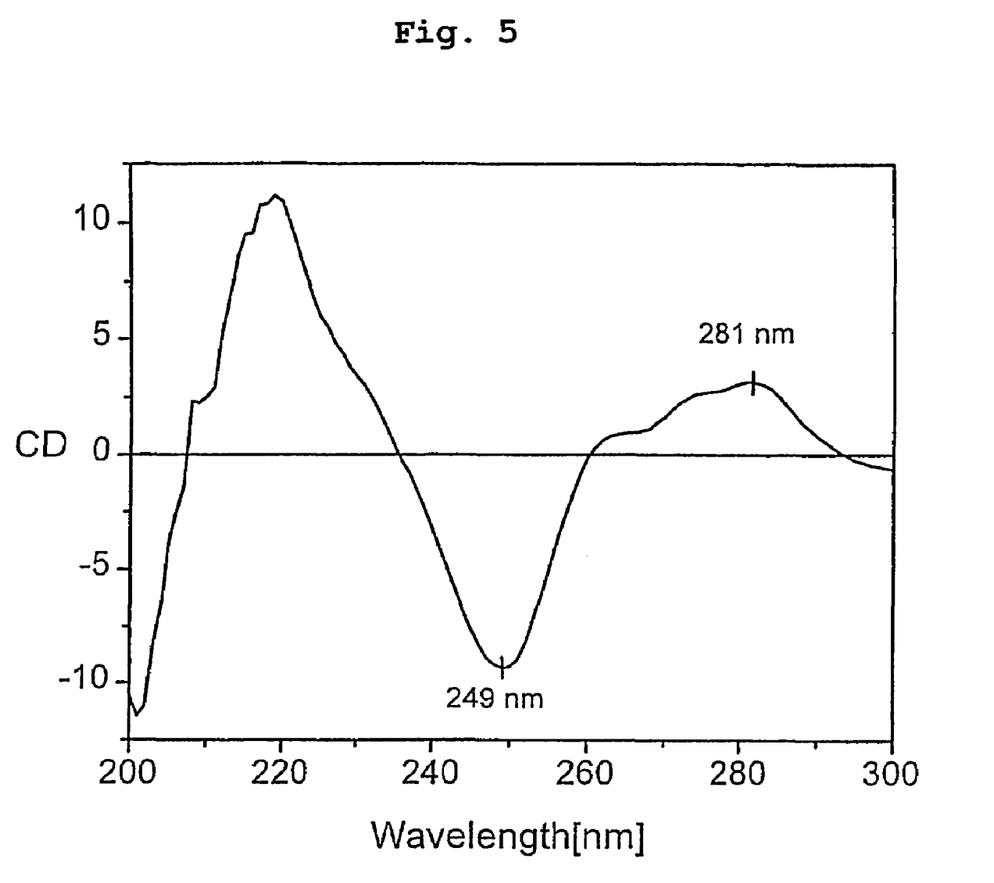
FIG. 5: CD spectrum of the inventive calix[4]arene-oligonucleotide.

The result in FIG. 5 provides a strong evidence for double helix formation through hydrogen bonding between complementary nucleo-bases (A and T) and DNA hairpin structure of the calixoligonucleotide. Further, the CD spectrum of the calixoligonucleotide shows a positive band centred at 281 nm, a negative band centred at 249 nm, and the zero being around 260 nm. These are distinct characteristics of B-form DNA (A. Rodger, et al., Circular Dichroism & Linear Dichroism; Oxford: Oxford University Press, pp. 24–29, 1997) and suggest that the inventive calixoligonucleotide is indeed of a DNA hairpin structure.

While the embodiments of the subject invention have been described and illustrated, it is obvious that various changes and modifications can be made therein without departing from the spirit of the present invention which should be limited only by the scope of the appended claims.

SEQUENCE LISTING

```
<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: calix[4]arene-oligonucleotide hybrid 1
<220> FEATURE:
<221> NAME/KEY: misc_feature
<222> LOCATION: (13)
<223> OTHER INFORMATION: calix[4]arene-nucleoside of chemical formula 1

<400> SEQUENCE: 1
aaaaaaaaaa aanttttttt ttttt                                            25

<210> SEQ ID NO 2
<211> LENGTH: 25
<212> TYPE: DNA
<213> ORGANISM: Artificial Sequence
<220> FEATURE:
<223> OTHER INFORMATION: calix[4]arene-oligonucleotide hybrid 2
<220> FEATURE:
<221> NAME/KEY: misc_feature
<222> LOCATION: (13)
<223> OTHER INFORMATION: calix[4]arene-nucleoside of chemical formula 1

<400> SEQUENCE: 2
tttttttttt ttnttttttt ttttt                                            25

<210> SEQ ID NO 3
<211> LENGTH: 25
<212> TYPE: DNA
<213> ORGANISM: Artificial Sequence
<220> FEATURE:
<223> OTHER INFORMATION: calix[4]arene-oligonucleotide hybrid 3
<220> FEATURE:
<221> NAME/KEY: misc_feature
<222> LOCATION: (13)
<223> OTHER INFORMATION: calix[4]arene-nucleoside of chemical formula 1

<400> SEQUENCE: 3
aaaagatatc aanttgacat ctttt                                            25
```

What is claimed is:

1. A calix[4]arene-nucleoside hybrid having at least one nucleoside attached to a calix[4]arene moiety through amide bonding, said moiety being derived from a calix[4]arene having one or more amino groups.

2. The calix[4]arene-nucleoside hybrid of claim 1, wherein the nucleoside is thymidine and the claix[4]arene has two amino groups.

3. The calix[4]arene-nucleoside hybrid of claim 1, which is selected from the group consisting of compounds of formula 1 to 4:

<Formula 1> where R = H, R' = H,

<Formula 2> where R = TBDMS, R' = TBDPS,

<Formula 3> where R = TBDMS, and

<Formula 4> where R = TBDPS.

4. A calix[4]arene-oligonucleotide hybrid having a moiety derived from the calix[4]arene-nucleoside hybrid of claim 1 and one or more nucleotide sequences, wherein the calix[4]arene-nucleoside hybrid has two nucleoside residues and the nucleotide sequences are respectively attached to the two nucleoside residues.

5. The calix[4]arene-oligonucleotide hybrid of claim 4, which is 5'-$A_{12}$-X-$T_{12}$3' of SEQ ID NO: 1, wherein A, T and X denote adenine, thymine and the calixf[4]arene-oligonucleoside hybrid of formula 1, respectively:

where R = H, R' = H.

6. The calix[4]arene-oligonucleotide hybrid of claim 5, which has the hairpin structure of Structural formula 1:

8. The calix[4]arene-oligonucleotide hybrid of claim 7, which has the hairpin structure of Structural formula 2:

wherein X denotes calix[4]arene-nucleoside of formula 1, and
the dots denote hydrogen bonds.

7. The calix[4]arene-oligonucleotide hybrid of claim 4, which is 5'-$T_{12}$-X-$T_{12}$-3' of SEQ ID NO: 2, wherein T and X denote thymine and the calix[4]arene-oligonucleoside hybrid of formula 1, respectively:

wherein X denotes calix[4]arene-nucleoside of formula 1, and
the dots denote hydrogen bonds.

9. The calix[4]arene-oligonucleotide hybrid of claim 4, which is 5'-AAAAGATATCAA-X-TTGACATCTTTT-3' of SEQ ID NO: 3, wherein A. T. G C and X denote adenine, thymine, guanine, cytosine and the calix[4]arene-oligonucleoside hybrid of formula 1, respectively:

<Formula 1> where R = H, R' = H.

10. The calix[4]arene-oligonucleotide hybrid of claim 9, which has the hairpin structure of Structural formula 3:

<Structural formula 3> wherein X denotes calix[4]arene-nucleoside of formula 1, and
the dots denote hydrogen bonds.

11. A method for preparing the calix[4]arene-nucleoside hybrid of claim 1, which comprises reacting calix[4]arene and a nucleoside derivative having a 3'- or 5'-carboxylic acid group to form an amide bond between an amino group of calix[4]arene and the carboxylic acid group of the nucleoside derivative.

12. The method of claim 11, wherein the nucleoside derivative is a thymidine derivative and the carboxylic acid group of the thymidine derivative is activated by adding a coupling agent and reacted with 1,3-diaminocalix[4]arene.

13. The method of claim 11, which further comprises the step of removing TBDMS and/or TBDPS protecting groups of calix[4]arene-nucleoside derivatives by treating with tetrabutylammonium fluoride.

14. The method of claim 12, wherein the coupling agent is selected from the group consisting of $(COCl)_2$, EDC (1-(3-dimethylaminopropyl)-3-ethylcarbodiimide hydrochloride), TBC (2,4,6-trichlorobenzoylchloride) and TBTU (O-benzotriazole-1-yl-N,N,N',N'-tetramethyluronium tetrafluoroborate).

15. A method for preparing the calix[4]arene-oligonucleotide hybrid of claim 4, which comprises the steps of synthesizing a DMTr protected 2-cyanoethyl phosphoroamidite building block of calix[4]arene-nucleoside of formula 1 and subjecting the block to solid phase oligonucleotide synthesis protocols.

* * * * *